United States Patent [19]
Offutt

[11] Patent Number: 5,712,917
[45] Date of Patent: Jan. 27, 1998

[54] SYSTEM AND METHOD FOR CREATING AUDITORY SENSATIONS

[75] Inventor: George Offutt, Green Lane, Pa.

[73] Assignee: George C. Offutt, Green Lane, Pa.

[21] Appl. No.: 344,182

[22] Filed: Nov. 22, 1994

[51] Int. Cl.[6] .................................................. H04R 25/00
[52] U.S. Cl. ............................ 381/68.6; 381/68; 381/151
[58] Field of Search ............................... 381/68.6, 68.3, 381/151, 68, 69, 68.2

[56] References Cited

U.S. PATENT DOCUMENTS

| | | | |
|---|---|---|---|
| 454,313 | 6/1891 | Webb | 381/151 |
| 651,472 | 6/1900 | Tindall . | |
| 662,278 | 11/1900 | Levalley . | |
| 3,108,268 | 10/1963 | Uttal | 381/151 |
| 3,751,605 | 8/1973 | Michaelson | 179/107 |
| 3,752,939 | 8/1973 | Bartz | 179/107 |
| 4,063,048 | 12/1977 | Kissiah, Jr. | 381/68.3 |
| 4,510,936 | 4/1985 | Fourcin et al. | 128/419 |
| 4,581,491 | 4/1986 | Boothroyd | 381/68 |
| 4,617,913 | 10/1986 | Eddington | 128/1 R |
| 4,729,366 | 3/1988 | Schaefer | 128/1.6 |
| 4,741,344 | 5/1988 | Danby et al. | 128/642 |
| 4,791,620 | 12/1988 | Leysieffer et al. | 381/68.2 |
| 4,850,962 | 7/1989 | Schaefer | 600/25 |

FOREIGN PATENT DOCUMENTS

| 2825233 | 1/1979 | Germany | 381/68.6 |
|---|---|---|---|

OTHER PUBLICATIONS

George Offutt, *The Electromodel of the Auditory System* (1984). See especially pp. 6–9, 12–15 and 154–158.

*Primary Examiner*—Sinh Tran

[57] ABSTRACT

Sound sensations are produced in the ear of a user by contacting the surface of the ear canal with an electrode and applying, between the electrode and another area of the user's body, electrical signals representing sounds to be heard. Preferably the electrode is mounted on an ear mold and a lead connected to the electrode, the lead extending through the mold to a source of audio electrical signals. The source may be a microphone on the ear mold.

2 Claims, 3 Drawing Sheets

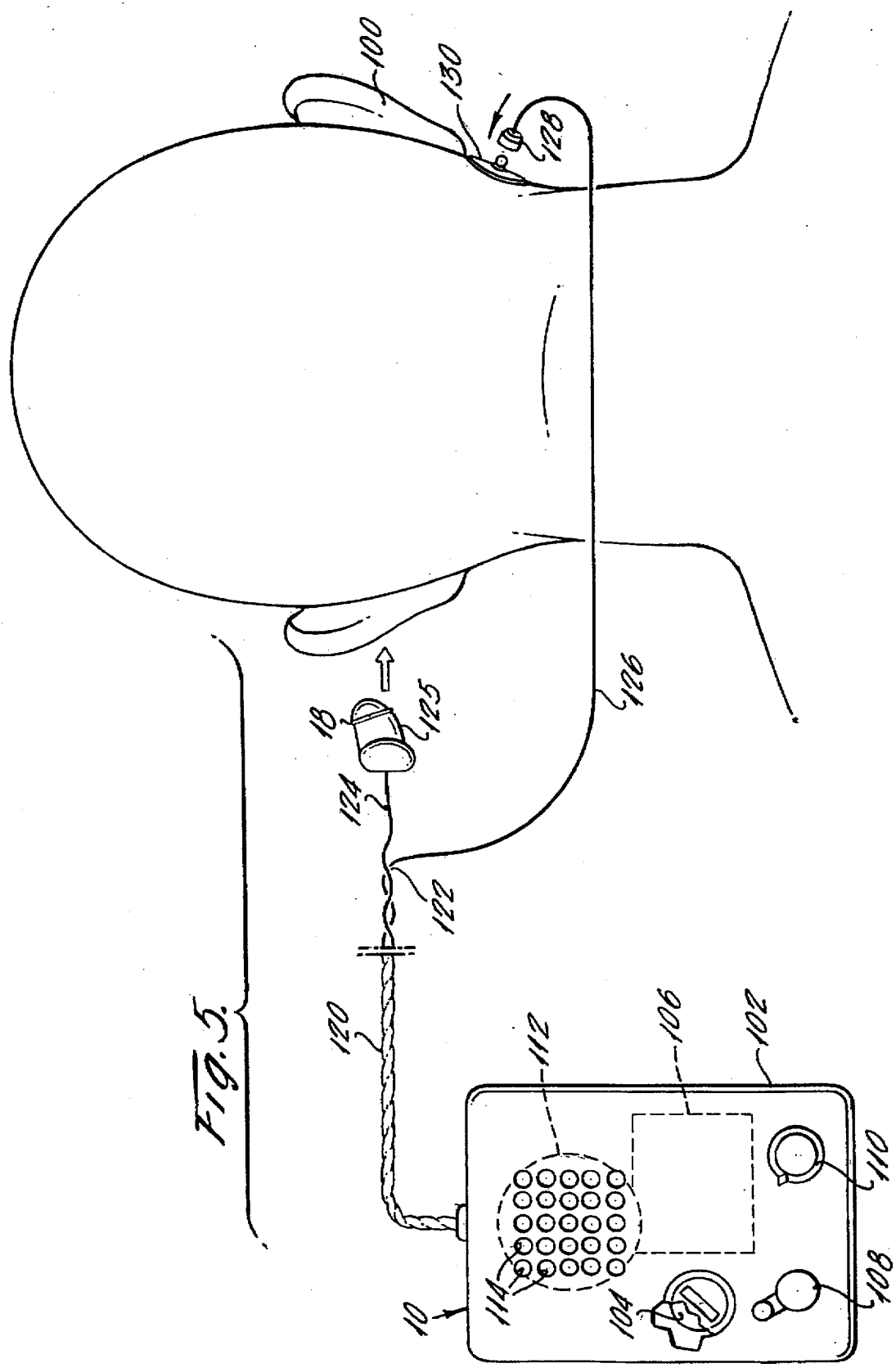

5,712,917

SYSTEM AND METHOD FOR CREATING AUDITORY SENSATIONS

FIELD OF THE INVENTION

This invention relates to systems for creating sound sensations in the ear; it relates particularly to electrically-operated hearing aids of the type which extend into the exterior ear canal.

BACKGROUND OF THE INVENTION

Persons with impaired hearing have, in the distant past, been aided in their hearing by a sound-wave collector such as ear trumpets; later, electrically operated hearing aids appeared, such as those applying mechanical vibrations to the bone near the ear (bone conduction hearing aids) and the now-usual hearing aid using an acoustic transducer mounted in the ear canal and driven by a microphone. It is also known that some degree of sound recognition can be achieved by implanting wires in the cochlea of the inner ear of deaf persons, and supplying electrical signals to the remote ends of the wires; such systems are not only very limited in their ability to provide reasonable sound detection and discrimination, but also are highly invasive, not only with respect to the delicate surgical implantation procedure required, but also with respect to the likely adverse long-term effects of the presence of the implant in the delicate and sensitive inner ear.

The most common hearing aid at the present time is the well-known acoustic transducer mounted in the ear canal by an ear mold, which transmits toward the eardrum acoustic waves corresponding to electrical signals supplied to it from a microphone device attached to the ear mold, or remotely located but connected to the transducer by appropriate electrical leads via any form of electrical amplifier which may be necessary for the particular user; a volume control and a supply battery are usually also provided to power the amplifier and adjust its output level.

While suitable and helpful in many cases, this conventional type of acoustic hearing aid itself has substantial drawbacks, as will now be described.

It is common knowledge that loud sounds in an environment may lead to a loss of hearing. Similarly, the level of sound reaching the inner ear from a conventional sonic hearing aid may be made so high that it can cause further damage to the function of the ear. Such losses due to loud sounds at the inner ear are often correlated with loss of the outer hair cells in the cochlea; it has also been suggested that the loss is due at least in part to pull-up of the tectorial membrane, in the case of low-intensity hearing loss.

Another problem often encountered relates to what is known as summation. This problem can occur in patients having significant hearing loss at low levels of auditory stimulation but a much better or even normal response to higher levels of stimulation. In such individuals there is generally a very narrow range of intensities between the level of sound detection and the level of pain.

It is an object of this invention to provide a new system and method for stimulating auditory sensations in the ear, especially at the hearing centers of a hearing-impaired person.

Another object is to provide such a system and method which does not involve an invasive installation, and in fact makes possible very easy installation and removal.

A further object is to provide such a system and method which do not require application of potentially harmful levels of sound to the middle or inner ear.

It is also an object to provide such a system and method which are simple and inexpensive, particularly in that no sound projector is required.

SUMMARY OF THE INVENTION

The present invention provides a new and useful hearing aid system utilizing direct electrical stimulation of the ear canal. It comprises a pair of electrodes, one of which makes contact with the ear canal (external meatus) and the other of which makes contact with another part of the user's body, i.e. the surface of the skin of the user; electrical signals representing sound are applied between the two electrodes, resulting in a direct electrical stimulation of the ear canal by the sound-representing electrical signals and a corresponding stimulation of the hearing system of the user, which is perceived by the user as sound.

The source of the electrical signals may be a microphone system, usually including a suitable electronic amplifier and volume control, which may be mounted in or on an ear mold also carrying the canal-contacting electrode and urging it against the canal surface; or, instead, a microphone, amplifier and volume control may be positioned remotely, but connected to the two conductors. The electrode which contacts the ear canal is preferably inert and biocompatible. Other sources of sound, such as sound recordings or radio signals, may be used instead of a microphone.

In a preferred embodiment, the portion of the conductor which contacts the ear canal is in the form of a ring, circumscribing the end portion of an ear mold, and pressed against the ear canal to produce an annular contact between the conductor and the interior surface of the ear canal.

BRIEF DESCRIPTION OF THE DRAWINGS

Various objects and features of the invention will be more readily apparent from a consideration of the following detailed description of preferred embodiments, taken with the accompanying drawings, in which:

FIG. 5 is an elevational view showing an alternative embodiment of the invention, in which the microphone and amplifier are in a unit remote from the ear canal, but electrically connected to it.

DETAILED DESCRIPTION OF PREFERRED EMBODIMENTS

Figure 1:
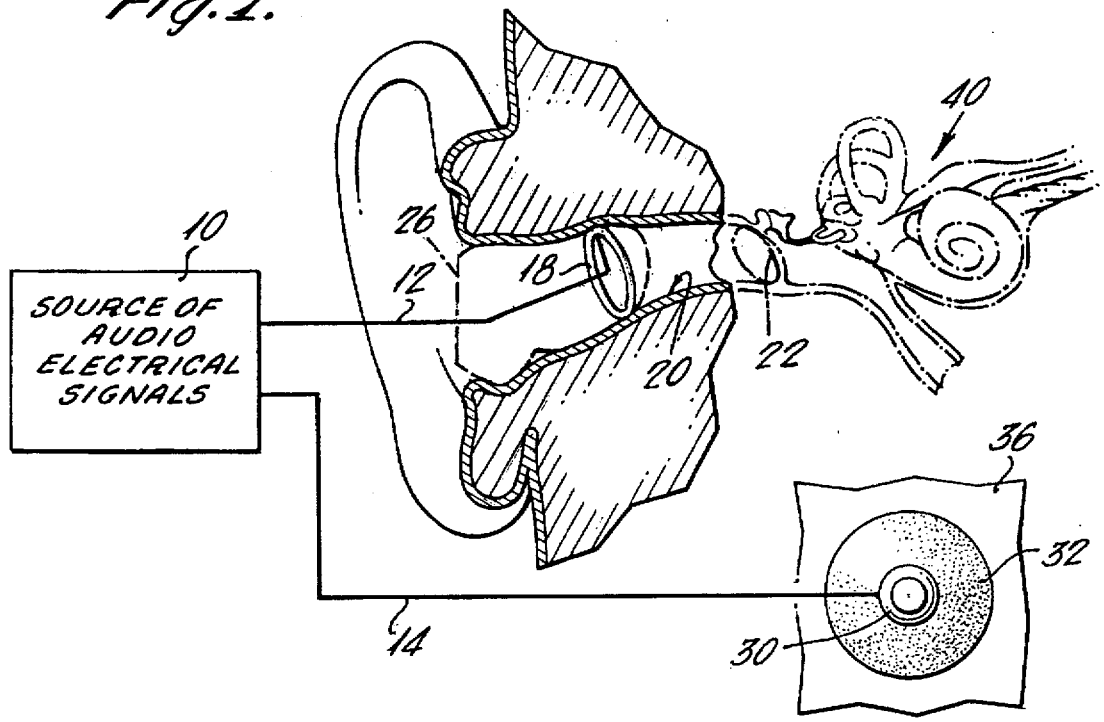
FIG. 1 is a partially schematic depiction of a complete system making use of the invention in one of its preferred forms.

Referring now to the generalized diagram of FIG. 1, there is shown a source 10 of audio electrical signals, that is, electrical signals having frequency components in the audio frequency band. The source may take many different forms, including but not limited to a microphone and amplifier, a sound recording system or radio, a source of a coded audio signal, etc., the level of the sound signal being suited and adjusted to the needs of the user. The output of the source is presented across output lines 12 and 14. Line 12 is connected to an electrode 18 which contacts the surface of the ear canal 20 of a user, external to the eardrum 22; broken lines 26 indicate schematically any suitable arrangement for supporting the electrode 18 in place against the ear canal. The other output lead 14 is connected to a quick-disconnect contact 30 which is in turn connected to a skin-contacting electrode 32 of conventional type, which typically includes an electrolytic solution for maintaining good electrical contact with the skin 36 and a suitable conventional cement for adhering it to the skin. This contacting system may be like that used in applying monitoring electrodes to the skin in making electrocardiograms, for example. The electrode 32 may be applied to any of a variety of areas of the skin of the user; for best operational results it is presently preferred to apply it to the skin of a contralateral area near the base of the neck, although the wrist on the same side of the body as the canal 20, or even the adjacent ear, are among convenient locations which can be used.

The audio electrical signals from source 10, applied between ear canal and skin, produce sound sensations in the inner ear 40 corresponding to the audio variations in the source signals, despite defects in the intervening structures such as the ear drum and ossicles, and despite pathological impediments in the intervening regions, thus enabling a user whose inner ear and auditory nerve structures are functional to enjoy the benefits of sound sensation.

The system may also be used to generate sound responses in the inner ear which counteract undesired acoustic sounds. It has been found that if an acoustic wave at a given audio frequency is projected through the ear canal, even in a normal ear, and an electrical audio signal of the same frequency but opposite phase is applied to an electrode which contacts the ear canal in sufficient amplitude, the effects of the electrical signal on the inner ear will oppose and substantially cancel the effects of the acoustic signal, making the system useful in deleting undesired sounds which otherwise might be distracting, harmful to the ear or unpleasant.

Figure 2:
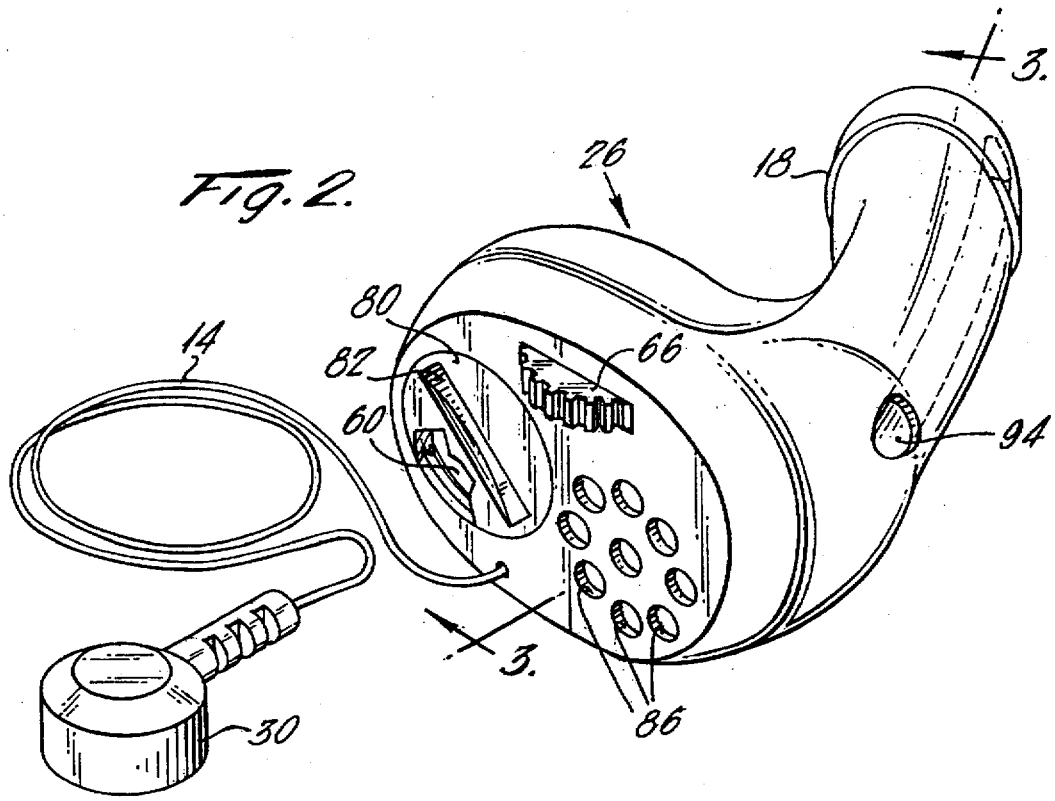
FIG. 2 is an enlarged perspective view of a preferred embodiment of the invention, shown in more detail.
Figure 3:
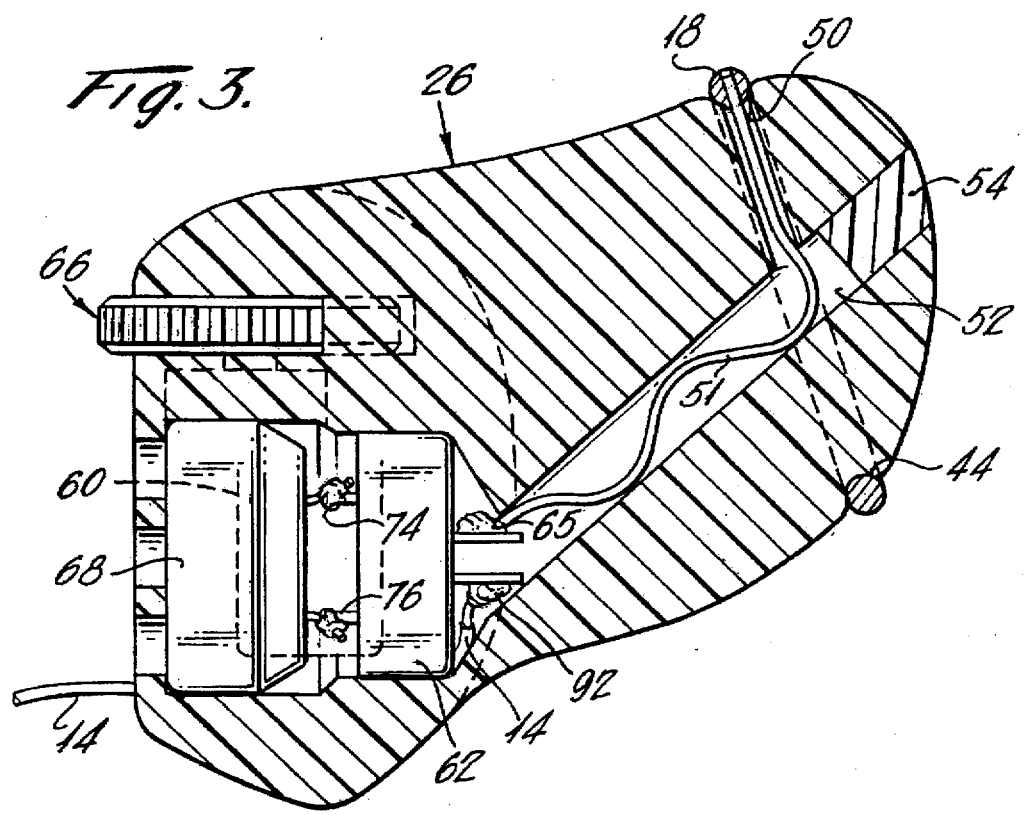
FIG. 3 is a vertical sectional view taken along lines 3—3 of FIG. 2.

FIGS. 2 and 3 illustrate more specifically a presently-preferred embodiment of the invention, wherein parts corresponding to FIG. 1 are designated by the same numerals. The electrode 18 is a silver wire one turn of which is located in a groove 44 (FIG. 3) near the end of the molded earplug 26 which is located innermost in the ear canal 20. The outer surface of the electrode 18 protrudes slightly outward of the earplug so that when the earplug (which has previously been molded to fit tightly into the ear canal) is inserted, the electrode makes reliable contact with the inner surface of the ear canal, external to the eardrum 22 (FIG. 1). A radial bore 50 (FIG. 3) provides a passage for a wire 51 which extends from electrode 18 to and through the longitudinal bore 52 to an amplifier signal output terminal 65. Wire 51 may be crimped into or otherwise electrically secured to electrode 18, or may be an integral extension of the ring-shaped electrode. In this example the earplug may be of a moldable plastic customarily used for hearing-aid earplugs, and in this example the external end of bore 52 is closed by a plastic plug 54.

Figure 4:
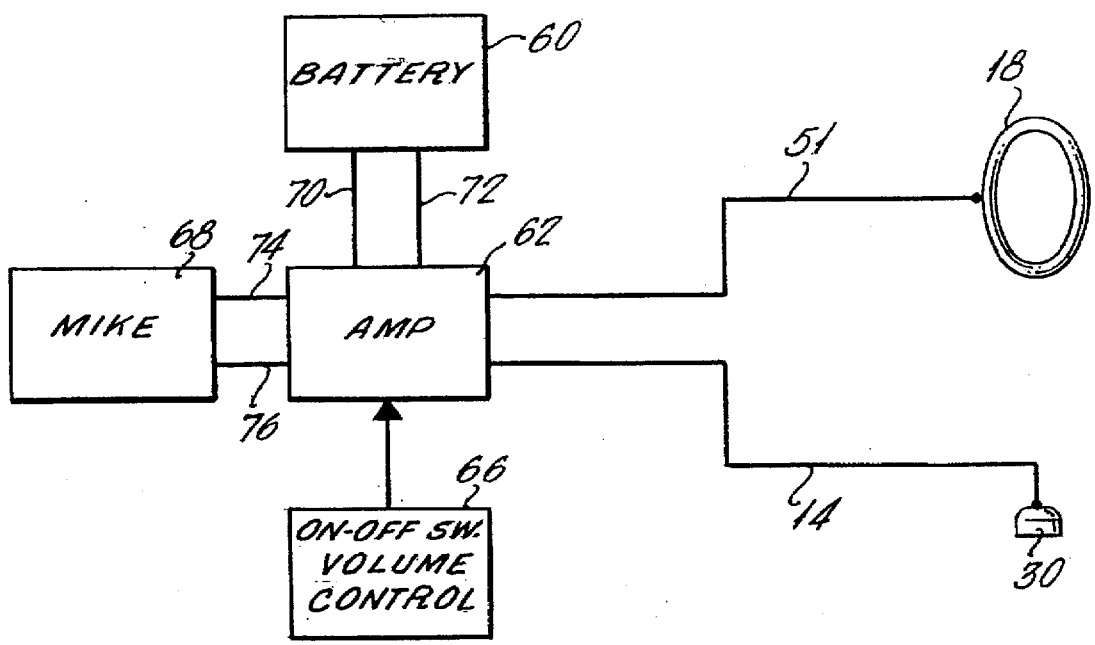
FIG. 4 is an electrical schematic diagram showing how the elements of FIG. 3 are connected together.

Also molded in place (see FIG. 3), by conventional hearing-aid techniques, are a battery 60, an adjustable amplifier 62, an on-off switch and volume control 66 and a pick-up microphone 68, electrically connected together as shown in FIG. 4; the battery supplies the power for the amplifier and microphone over leads 70, 72, the microphone being connected to the amplifier over leads 74, 76; the on-off switch and volume control 66 comprises a thumb-wheel mechanically connected to a usual switch and variable resistor in the amplifier. The battery is provided with an external threaded cover cap 80 (FIG. 2) having a slot 82 in its external surface for convenient turning to remove or replace it, thereby to obtain access to the battery for replacement. Holes such as 86 (FIG. 2) permit sound waves to pass easily from the exterior to the microphone. Electrical lead 14 is connected to the other amplifier output terminal 92 and passes through the ear mold to the exterior, where it is connected to the conventional connector contact 30.

In this example a bore 94 extends longitudinally through the earplug (see FIG. 2); one end of the bore opens to the surface of the earplug exterior to the parts of the earplug which contact the ear canal, and the other end extends to the surface on the opposite side of the canal-contacting portion of the earplug. This provides an air passage around the portion of the earplug which contacts the ear canal, thus not only relieving any air-pressure differences on opposite sides of the earplug but also providing a parallel passage for acoustic waves to supplement the hearing sensation produced electrically by the system of the present invention.

The presently-preferred location for the "ground" or body electrode 32 is illustrated in FIG. 5, namely on the skin of the neck below the opposite ear 100. FIG. 5 illustrates an embodiment in which the source 10 of audio electrical signals comprises a stand-alone unit comprising a case 102 containing the battery 104, the amplifier 106, an on-off switch 108, a volume control 110 and a microphone 112 located behind holes 114 in the case. The two output leads of the amplifier 106 constitute a twisted pair 120 extending from the case. The case may be designed to be placed on a surface or in a pocket, or to be clipped to the user's clothing. At 122 the pair separates into the signal or "hot" lead 124 and the "ground" or reference lead 126. Signal lead 124 is connected to the canal-contacting electrode 18 on modified earplug 125, and the reference lead 126 is connected to the contact 128 which snaps onto the electrode 130 on the opposite side of the neck. This type of system permits use of larger and more varied circuit elements then when all elements must be incorporated into an earplug, and also permits use of a very small, nearly-invisible support for the canal contacting electrode which, alternatively to the ring, may be a small plug of resilient wire mesh, or a springy or rubbery body coated at least partly with an electrically conductive material.

Thus many variations of the system of the invention will occur to one skilled in the art.

While not seeking to be bound by the details of any particular theory of operation of the invention, it is believed that the electrical signals applied to the external ear canal by the signal electrode produce sensations, thus bypassing the eardrum and the middle ear where pathological conditions impairing normal nearing may be present.

The strength of the electrical signals applied to the ear canal depends upon factors such as the placement of the reference electrode, the excellence of contact which the reference electrode makes to the skin, the area of contact between signal electrode and ear canal and the condition of the inner ear, especially the inner hair cells, of the user; also to be considered are the severity of the user's disfunction. In general, the system suitably provides a maximum of a few milliamperes of current to the ear canal, which the user can then turn down to a suitable comfortable level by operation of the amplifier volume control.

In another application the system may be used in conjunction with ear muffs or ear protectors, where it is desired to block out ambient sound, and permits desired electrical communicating to the user, as by a radio connected to the signal electrode despite the interfering noises. It may also be used in analyzing injury to the ear, by comparing the patient's response to sonic ear input to that produced by electrical stimulation of the ear canal according to the invention, thereby to obtain indications of whether mechanical conduction of sonic vibration is a problem.

It is further contemplated that the earplug may be constructed to provide not only the electrical stimulation of the ear canal described above, but also sonic stimulation, when desired, by including in the earplug a speaker connectable to a source of audio frequency signals. This embodiment is not only useful for the testing described above, but may also be used as a hearing aid for the general use of those who prefer to receive both electrical and sonic stimulation from their hearing aid, and also if desired direct sonic stimulation via the ambient by way of the passage 94 in FIG. 2.

While the invention has been described with particular reference to specific embodiments in the interest of complete definiteness, it will be understood that it may be embodied in a variety of forms diverse from those specifically shown and described, without departing from the spirit and scope of the invention.

What is claimed is:

1. A system for providing auditory effects in the ear of a user comprising:

an electrode structure;

means for mounting said electrode structure in contact with the ear canal of the user, said means for mounting said electrode structure includes an ear mold on which said electrode structure is supported, said electrode structure includes an annular ring that extends over a surface portion of said ear mold adjacent to the end thereof which is adapted to fit farthest into the ear canal; and means for applying electrical stimulation that corresponds to audio signals to said electrode structure.

2. The system of claim 1, wherein said means for applying electrical signals comprises an electro-acoustic transducer mounted on said ear mold, the electrical output of said transducer being connected to said electrode structure.

* * * * *